United States Patent [19]
Caretto et al.

[11] Patent Number: 6,130,210
[45] Date of Patent: Oct. 10, 2000

[54] HEPARIN DERIVATIVES HAVING ANTIMETASTATIC ACTIVITY

[75] Inventors: Patrizia Caretto; Teresa Sciumbata; Flavio Leoni; Gianni Gromo, all of Sesto S. Giovanni, Italy

[73] Assignee: Italfarmaco S.p.A., Milan, Italy

[21] Appl. No.: 09/050,996

[22] Filed: Mar. 31, 1998

Related U.S. Application Data

[62] Division of application No. 08/591,575, filed as application No. PCT/EP94/02133, Jun. 30, 1994, Pat. No. 5,763,421.

[30] Foreign Application Priority Data

Jul. 12, 1993 [IT] Italy .................................. MI93A1518

[51] Int. Cl.[7] .......................... A61K 31/725; C08B 37/10
[52] U.S. Cl. ................................................. 514/56; 536/21
[58] Field of Search .................. 514/56; 536/21

[56] References Cited

U.S. PATENT DOCUMENTS

| | | | |
|---|---|---|---|
| 4,816,446 | 3/1989 | Feller et al. | 514/56 |
| 4,933,326 | 6/1990 | Bianchini et al. | 514/56 |
| 4,990,502 | 2/1991 | Lormeau et al. | 514/56 |
| 5,541,166 | 7/1996 | Parish et al. | 514/56 |
| 5,795,860 | 8/1998 | Witt et al. | 514/12 |

*Primary Examiner*—Kathleen K. Fonda

[57] ABSTRACT

Heparin derivatives are disclosed that may be used to inhibit formation of metastases. One series of heparin derivatives of the invention are N-acylated with monocarboxylic acids or dicarboxylic acids and have molecular weights from about 1000 Daltons to about 30,000 Daltons. Another series of heparin derivatives of the invention have average molecular weights ranging from about 1000 to 3000 daltons, and are optionally N-acylated with residues from aliphatic monocarboxylic or dicarboxylic acids.

15 Claims, No Drawings

HEPARIN DERIVATIVES HAVING ANTIMETASTATIC ACTIVITY

This is a division of application Ser. No. 08/591,575, filed Mar. 5, 1996, now U.S. Pat. No. 5,763,421, which is in turn a U.S. national stage entry under 35 U.S.C. § 371 of PCT/EP94/02133, filed Jun. 30, 1994.

The present invention relates to heparin derivatives, particular heparin fragments and fractions, and the use thereof as antimetastatic agents.

The antimetastatic activity of heparin has been known for some time (see, for example, Drago, J. R. et al., Anticancer Res., 4(3), 171-2, 1984), although some authors doubt its real efficacy in this field, assigning it, on the contrary, with a metastases-stimulating effect (see, for example, S. Y. Chan, and M. Pollard, J.N.C.I., 64, n. 5, May 1980). Low molecular weight heparin also has antimetastatic activity, which some authors consider higher than that of normal heparin (Green, D. et al. The Lancet, 339, Jun. 13, 1992). Nevertheless, the use of said molecules in this field is severely restricted by the marked anticoagulant and antithrombotic activities thereof.

Subsequently, studies have been directed to heparin derivatives. For example, WO 88/05301 reports data about the antimetastatic activity of heparin, of N-desulfated N-acetylated heparin and of oxidized-reduced heparins: heparin as such turns out to be the mainly active compound, whereas its derivatives have quite a lower effect, reducing the number of metastases by about 40–50%.

It should be noted, anyway, that N-desulfated N-acetylated heparin shows antithrombotic and fibrinolytic effects which could restrict its use as an antitumoral (see, EP-A-0 413 248).

An object of present invention relates to the use of heparin derivatives, or of fragments and fractions thereof, having a molecular weight ranging from 1,000 to about 30,000 Da, N-acylated with residues from aliphatic monocarboxylic acids having 3 to 20 carbon atoms, or with residues from aliphatic dicarboxylic acids having 3 to 10 carbon atoms, and having a N-acylation degree, defined as the percent ratio of the number of N-acylated residues to the number of N-sulfated groups present in the heparin compound which they derive from, ranging from about 10 to about 100, and the salts thereof, as antimetastatic compounds.

A further object of present invention is the use of particular heparin fragments or fractions having an average molecular weight equal or lower than 3,000 Da, and the salts thereof, as antimetastatic compounds. By aliphatic monocarboxylic acid residues having 3 to 20 carbon atoms, residues are meant such as those from propionic, butyric, caproic, caprylic, capric, lauric, myristic, palmitic, stearic, crotonic, oleic, elaidic, stearolic, tetrolic, arachic acids and analogues. By aliphatic dicarboxylic acid residues having 3 to 10 carbon atoms, residues such as those from malonic, succinic, dimethylmalonic, glutaric, suberic, azelaic and sebacic acids and analogues are meant. These mono- or dicarboxylic acids can also be substituted with one or more hydroxy, amino or acylamino groups, thus obtaining, for example, heparins N-acylated with residues from lactic, hydracrylic, tartaric, tartronic, malic, aspartic, glutamic, N-acetylaspartic, N-acetylglutamic acids and the like.

The heparin derivatives of present invention are commercially available products or they are prepared according to procedures well-known to those skilled in the art, or described in scientific and patent literatures.

The procedures for the synthesis of partially or completely N-desulfated and N-acylated heparin derivatives are disclosed in U.S. Pat. No. 3,118,816, in WO 92/22588 (in the name of ITALFARMACO S.P.A.) and in GB Patent 2,078,768.

The heparin fragments of average molecular weight equal or lower than 3,000 D are prepared according to the procedures described by Riesenfeld J. and Rodén L., Anal. Biochem., 188, 383–389 (1990), and by Shively J. E. and Conrad E., Biochemistry, 15, N. 18, 3932–3942 (1976).

The following examples further illustrate the invention without limiting it.

EXAMPLE 1

100% N-Succinylated N-Desulfated Heparin a) N-Desulfated Heparin.

The preparation was carried out according to the procedure by Lloyd et al., Biochem. Pharm., 30, 637–648, 1971. An aqueous solution containing 1.1 g of porcine sodium heparin [Average MW—13,600 Da; anti-Xa activity—206 U/mg (chromogenic); APTT—202 U/mg)] was percolated through a column thermostatized at 4° C., containing 50 ml of Dowex® 50 W×8H cationic resin. The eluate (50 ml) containing the heparin acid, pH about 2, was placed into a round-bottom flask at 55° C. for 24 hours, under mild stirring, at constant temperature. The solution was cooled to room temperature, neutralized to pH 7 with 1N NaOH, then freeze-dried to obtain the title product in form of a white powder. The desulfation degree was >95%, in agreement with the $^{13}$C-NMR analysis (shift of the $C_1$ signal of the amino sugar from 99.5 to 94 ppm, and shift of the $C_2$ signal from 60.5 to 66.8 ppm).

b) The product obtained in a) was dissolved in 100 ml of water (1% solution) under stirring. The solution was neutralized with 0.1N NaOH, and 2 g of solid succinic anhydride was added in 250 mg aliquots, always at room temperature. Each addition required pH to be adjusted from 5 to 7 with 0.1N NaOH. At the end of the reaction, the insoluble succinate excess was filtered off, and the resulting clear solution was treated with 3 volumes of absolute ethanol, to obtain a white, solid precipitate, which was washed with absolute ethanol, then redissolved in water (5% solution), and the resulting solution was placed into dialysis membrane (SPECTRAPOR® with cut-off 8,000 D) for 24 hours, against 2 l of water. The intradialysis solution was freeze-dried, to obtain the title product in form of white powder, having the following characteristics.

Sulfates/carboxyls—0,91

Electrophoresis in barium acetate: $R_f$—unitary spot

Electrophoresis in HCl: $R_f$=0.61

Anti-Xa activity<1 U/mg

APTT—26.4 U/mg

Average MW (HPLC)—13,300 Da

Non-sulfated uronic acids (NMR)—25.6%

EXAMPLE 2

50% N-Succinylated N-Desulfated Heparin

Following the procedure described in Example 1a), but effecting the reaction at 40° C. for 24 hours, a partially N-desulfated (>50%) heparin derivative was obtained, which desulfation degree was checked by means of $^{13}$C-NMR analysis as above described, and which was subjected to a succinylation reaction as described in Example 1b). The product, obtained in form of a white powder, has the following characteristics.

Sulfates/carboxyls—1.2
Electrophoresis in barium acetate: $R_f$=2 spots
Electrophoresis in HCl: $R_f$=0.64
Anti-Xa activity<1 U/mg
APTT=18.3 U/mg
Average MW (HPLC)—13,300 Da
Non-sulfated uronic acids (NMR)—39.7%

EXAMPLE 3

30% N-Succinylated N-Desulfated Heparin

Following the procedure described in Example 1a), but effecting the reaction at 35° C. for 24 hours, a partially N-desulfated (>30%) heparin derivative was obtained, which was subjected to a succinylation reaction as described in Example 1b). The product, obtained in form of a white powder, has the following characteristics.

Sulfates/carboxyls—1.44
Electrophoresis in barium acetate: $R_f$—2 spots
Electrophoresis in HCl: $R_f$=0.68
Anti-Xa activity—19.5 U/mg
APTT—74.8 U/mg
Average MW (HPLC)—13,300 Da
Non-sulfated uronic acids (NMR)—30.4%

EXAMPLE 4

100% N-Succinylated Low Molecular Weight Heparin

The procedure described in Example 1 was followed, starting from 1 g of a low molecular weight heparin (Average MW—5,000 Da; anti-Xa activity—97 U/mg; APTT—74 U/mg; Calbiochem). The purification of the N-succinylated derivative from the succinate excess was carried out in a dialysis membrane SPECTRAPOR® with cut-off 1,000 D, according to what described in Example 1b). After freeze-drying, the title product is obtained in form of a white powder having the following characteristics.

Sulfates/carboxyls=1
Electrophoresis in barium acetate: $R_f$=unitary spot
Electrophoresis in HCl: $R_f$=0.62
Anti-Xa activity<1 U/mg
APTT—4.9 U/mg
Average MW (HPLC)—4,070 Da
Non-sulfated uronic acids (NMR)—34.5%

EXAMPLE 5

50% N-Succinylated Low Molecular Weight Heparin

Following the procedure described in Example 2, starting from 1 g of the heparin derivative used in Example 4, the title product is obtained in form of a white powder, having the following characteristics.

Sulfates/carboxyls—1.1
Electrophoresis in barium acetate: $R_f$=unitary spot
Electrophoresis in HCl: $R_f$—0.66
Anti-Xa activity<1 U/mg
APTT<1 U/mg
Average MW (HPLC)—3,660 Da
Non-sulfated uronic acids (NMR)—38%

EXAMPLE 6

100% N-Succinylated Very Low Molecular Weight Heparin

The procedure described in Example 1 was followed starting from 1 g of a very low molecular weight heparin (Average MW<3,000 Da; anti-Xa activity>50 U/mg; APTT<45 U/mg; Sigma). The purification of the N-succinylated derivative from the succinate excess was carried out by fractional precipitation, making use of the selective formation of complexes with alkylammonium salts (see. Methods of Biochem. Anal., 8, 145–197, 1960): the 5% solution of N-succinylated very low molecular weight heparin was subjected to selective precipitation with 10% cetyl pyridinium chloride in the absence of salts, at 4° C., leaving to stand for about 2 hours, then centrifuging at 4,000×g for 20 minutes. The resulting precipitate was separated from the succinate excess in the solution, and after washing for 3 times with warm distilled water, was redissolved at 30–35° C. in a 2M NaCl solution. Said solution was treated with 3 volumes of absolute ethanol, to precipitate the title product, having the following characteristics.

Sulfates/carboxyls—0.9
Electrophoresis in barium acetate: $R_f$—unitary spot
Electrophoresis in HCl: $R_f$=0.74
Anti-Xa activity<1 U/mg
APTT—2.4 U/mg
Average MW (HPLC)—2,350 Da

EXAMPLE 7

50% N-Desulfated and N-Succinylated Very Low Molecular Weight Heparin

The procedure described in Example 2 was followed, starting from 1 g of the heparin derivative used in Example 6. The purification of the product was carried out as described in Example 6, to obtain a compound having the following characteristics.

Sulfates/carboxyls—1.1
Electrophoresis in barium acetate: $R_f$—unitary spot
Electrophoresis in HCl: $R_f$—0.78
Anti-Xa activity<1 U/mg
APTT<1 U/mg
Average MW (HPLC)—2,400 Da

EXAMPLE 8

50% N-Succinylated N-Desulfated Heparin Calcium Salt

The product of Example 2 (1 g) was percolated through a column thermostatized at 4° C., containing 50 ml of cationic resin DOWEX® 50WX8H⁺. The eluate containing the acid form of the intermediate was titred with a stoichiometric amount of calcium carbonate, and the solution was freeze-dried, to obtain the title product in form of a white powder, having the following characteristics.

Sulfates/carboxyls—1.2
Electrophoresis in barium acetate: $R_f$—2 spots
Electrophoresis in HCl: $R_f$32 0.64
Anti-Xa activity<1 U/mg
APTT—19 U/mg
Average MW (HPLC)—13,300 Da

EXAMPLE 9

50% N-Desulfated N-Succinylated Low Molecular Weight Heparin Calcium Salt

The product of Example 5 (1 g) was treated as described in Example 8, to obtain the title product having the following characteristics.

Sulfates/carboxyls—1.1
Electrophoresis in barium acetate: $R_f$=unitary spot
Electrophoresis in HCl: $R_f$=0.74
Anti-Xa activity<1 U/mg
APTT<1 U/mg
Average MW (HPLC)—3,660 Da

EXAMPLE 10

50% N-Desulfated N-Succinylated Very Low Molecular Weight Heparin Calcium Salt

The product of Example 7 (1 g) was treated as described in Example 8, to obtain the title product, having the following characteristics.

Sulfates/carboxyls—1.1
Electrophoresis in barium acetate: $R_f$—unitary spot
Electrophoresis in HC: $R_f$=0.78
Anti-Xa activity<1 U/mg
APTT<1 U/mg
Average MW (HPLC)—2,400 Da

EXAMPLE 11

100% Oxidized-Reduced N-Desulfated N-Succinylated Heparin a) 100% oxidized N-desulfated N-succinylated heparin.

A solution of 10 g of the product of Example 1 in 500 ml of 50 mM citric acid buffer, pH 3, added with 0.2M sodium perchlorate was cooled at 4° C. and mixed with a solution of 4.29 g of sodium metaperiodate in 500 ml of the same buffer, previously cooled at 4° C. The mixture was reacted under stirring, in the dark, for 24 hours at 4° C., keeping pH at 3. At the end of the reaction (checked by photometric reading at 223 nm), 100 ml of an aqueous solution containing 11 ml of ethylene glycol added, then the mixture was neutralized with 1N NaOH. The product was recovered by precipitation from absolute ethanol (yield: 90%).

b) 450 ml of an aqueous solution of 9 g of the product of step a) were added with 340 mg of sodium borohydride in 10 ml of water. The reaction mixture was left to react for 3 hours at room temperature, then the sodium borohydride excess was removed adjusting the solution to pH 5 with 1N HCl. After a night, the mixture was neutralized with 1N NaOH, and, by precipitation from 3 volumes of absolute ethanol, the product was recovered (yield: about 70%) having the following characteristics.

Sulfates/carboxyls—0.97
Electrophoresis in barium acetate: $R_f$=unitary spot
Electrophoresis in HCl: $R_f$=0.56
Anti-Xa activity<1 U/mg
APTT—21.9 U/mg
Average MW (HPLC)—11,000 Da
Non-sulfated uronic acids (NMR)—11.1%

EXAMPLE 12

30% Oxidized-Reduced N-Desulfated N-Succinylated Heparin

According to the procedure of Example 11, starting from 3 g of the compound of Example 3, the title product was obtained, having the following characteristics (yield: 10 g).

Sulfates/carboxyls—1.55
Electrophoresis in barium acetate: $R_f$—unitary spot
Electrophoresis in HCl: $R_f$—0.59
Anti-Xa activity<1 U/mg
APTT—29.0 U/mg
Average MW (HPLC)—9,500 Da
Non-sulfated uronic acids (NMR)=2%

EXAMPLE 13

100% Oxidized-Reduced N-Desulfated N-Succinylated Low Molecular Weight Heparin

According to the procedure of Example 11, starting from 17 g of the compound of Example 4, the title product is obtained, having the following characteristics (yield: 13 g).

Electrophoresis in barium acetate: $R_f$=unitary spot
Electrophoresis in HCl: Rf—0.59
Anti-Xa activity<1 U/mg
Average MW (HPLC)=4,000 Da
Non-sulfated uronic acids (NMR)=12.8%

EXAMPLE 14

Very Low Molecular Weight Heparin

A 2% solution (2 g in 100 ml) of porcine sodium heparin [Average MW—13,600 Da; anti-Xa activity—206 U/mg (chromogenic); activity APTT—202 U/mg)] was cooled to 4° C., and pH was adjusted to 2 with hydrochloric acid, then was added with a solution of 120 mg of sodium nitrite in 800 μl of water, quickly added. The pH was readjusted to 2, and the mixture was reacted for 15 minutes, then was neutralized with NaOH. 500 mg of 5 ml of sodium borohydride were added thereto and the mixture was left to react overnight, after that the sodium borohydride excess was removed, pH was adjusted to 5, then, when effervescence was over, pH was readjusted to 7. The title product is precipitate with 3 volumes of ethanol, and dried in oven, under vacuum, at 35° C.

Electrophoresis in barium acetate: $R_f$=unitary spot
Electrophoresis in HCl: $R_f$=0.73
Anti-Xa activity<1 U/mg
APTT—37 U/mg
Average MW (HPLC)—2,100 Da The compounds of present invention have antimetastatic and antiproliferative activities, therefore they are potentially useful in oncology. However, they are devoid of anti-angiogenic activity.

The antiproliferative and antimetastatic activities of the compounds will be illustrated by means of the following test:

INHIBITION OF METASTASES FORMATION

Ten female mice C57BL/6 (18–20 g weight) were inoculated subcutaneously with varying doses of some of representative compounds of the invention, then, after 10 minutes, they were inoculated intravenously with murine melanoma cells B16BL6 ($10^5$ cells/mouse). The animals were observed for 21 days, then they were killed. Following a general examination of the animal to evaluate the presence of any extra-pulmonary metastases, lungs were explanted, then fixed in a suitable solution to count metastases under stereoscopic microscopy. Only the tests in which the animals of the control groups showed an average metastases number higher than 100 were considered.

The compounds of present invention showed a percent inhibition of the metastases number always higher than 50%, at dosages generally higher or equal to 100 μg/mouse. Moreover, to further prove the antimetastatic activity, some compounds showed a 20% inhibition of the tumour taking hold at the same doses as above. In some representative tests, the compound of Example 11 showed a percent inhibition of the metastases number higher than 60%, at doses higher or equal to 200 μg/mouse, whereas the compound of Example 1 showed a slightly lower activity (about 50% percent inhibition of the metastases number) at the same doses.

The compound of Example 4 had a percent inhibition of the metastases number higher than 60% at doses higher than 200 μg/mouse, together with an inhibition of the tumour taking hold of about 20%. Finally, a commercial heparin having the following characteristics: Average MW<3,000 Da; anti-Xa activity>50 U/mg; APTT<45 U/mg; showed a percent inhibition of the metastases number higher than 80% at doses ranging from 100 to 400 μg/mouse, and a percent inhibition of the metastases number higher than 50%, at doses of 50 μg/mouse; moreover it showed a inhibition of the tumour taking hold of about 20% even at a dose of 50 μg/mouse.

The present invention relates to all the industrially applicable aspects related to the use of the claimed compounds claimed as therapeutical agents. Therefore, a main object of the present invention is provided by pharmaceutical compositions of said salts together with conventional excipients or carriers.

Particularly, a further object of the invention relates to pharmaceutical preparations suitable to the parenteral and oral administrations, containing therapeutically effective amounts of a compound of present invention. Said compositions can be prepared according to techniques known to those skilled in the art, as described, for example, in "Remington's Pharmaceutical Science Handbook", XVII Ed., Mack Pub., N.Y., USA. The dosology, anyway, will be chose by the clinician, depending on the severity of the pathology to treat and the conditions, weight, age and sex of the patient.

What is claimed is:

1. A method for Inhibition of formation of metastases in a patient affected with neoplasias which comprises the step of administering to said patient a therapeutically effective amount of a heparin derivative devoid of anti-angiogenic activity and having an average molecular weight ranging from about 1000 to about 30,000 daltons, N-acylated with residues from aliphatic monocarboxylic acids having 3 to 20 carbon atoms, or with residues from aliphatic dicarboxylic acids having 3 to 10 carbon atoms, and having an N-acylation degree ranging from about 10 to about 100, or salts thereof with alkali or alkaline-earth metal cations.

2. The method of claim 1, wherein the N-acyl group is succinoyl, the N-acylation degree is 100, and the heparin derivative has an average molecular weight of 13,300 daltons.

3. The method of claim 1, wherein the N-acyl group is succinoyl, the N-acylation degree is 50, and the heparin derivative has an average molecular weight of 13,300 daltons.

4. The method of claim 1, wherein the N-acyl group is succinoyl, the N-acylation degree is 30, and the heparin derivative has an average molecular weight of 13,300 daltons.

5. The method of claim 1, wherein the N-acyl group is succinoyl, the N-acylation degree is 100, and the heparin derivative has an average molecular weight of 4070 daltons.

6. The method of claim 1, wherein the N-acyl group is succinoyl, the N-acylation degree is 50, and the heparin derivative has an average molecular weight of 3660 daltons.

7. The method of claim 1, wherein the N-acyl group is succinoyl, the N-acylation degree is 50, and the heparin derivative is a calcium salt that has an average molecular weight of 13,300 daltons.

8. The method of claim 1, wherein the N-acyl group is succinoyl, the N-acylation degree is 50, and the heparin derivative is a calcium salt that has an average molecular weight of 3660 daltons.

9. A composition for inhibition of formation of metastases in a patient which comprises a therapeutically effective amount of a heparin derivative devoid of anti-angiogenic activity and having an average molecular weight ranging from about 1000 to about 30,000 daltons, N-acylated with residues from aliphatic monocarboxylic acids having 3 to 20 carbon atoms, or with residues from aliphatic dicarboxylic acids having 3 to 10 carbon atoms, and having an N-acylation degree ranging from about 10 to about 100, or salts thereof with alkali or alkaline-earth metal cations, admixed with a pharmaceutically acceptable carrier.

10. A method for inhibition of formation of metastases in a patient affected with neoplasias which comprises the step of administering to said patient a therapeutically effective amount of a heparin derivative devoid of anti-angiogenic activity and having an average molecular weight ranging up to 3000 daltons, optionally N-acylated with residues from aliphatic monocarboxylic acids having 3 to 20 carbon atoms, or with residues from aliphatic dicarboxylic acids having 3 to 10 carbon atoms, to an N-acylation degree ranging from about 10 to about 100, or salts thereof with alkali or alkaline-earth metal cations.

11. The method of claim 1, wherein the N-acyl group is succinoyl, the N-acylation degree is 100, and the heparin derivative has an average molecular weight of 2350 daltons.

12. The method of claim 1, wherein the N-acyl group is succinoyl, the N-acylation degree is 50, and the heparin derivative has an average molecular weight of 2400 daltons.

13. The method of claim 1, wherein the N-acyl group is succinoyl, the N-acylation degree is 50, and the heparin derivative is a calcium salt that has an average molecular weight of 2100 daltons.

14. The method of claim 10, wherein the heparin derivative has an average molecular weight of 2100 daltons.

15. A composition for inhibition of formation of metastases in a patient which comprises a therapeutically effective amount of a heparin derivative devoid of anti-angiogenic activity and having an average molecular weight ranging up to 3000 daltons, optionally N-acylated with residues from aliphatic monocarboxylic acids having 3 to 20 carbon atoms, or with residues from aliphatic dicarboxylic acids having 3 to 10 carbon atoms, to an N-acylation degree ranging from about 10 to about 100, or salts thereof with alkali or alkaline-earth metal cations, admixed with a pharmaceutically acceptable carrier.

* * * * *